United States Patent
Obel et al.

[19]

[11] Patent Number: 5,861,008

[45] Date of Patent: Jan. 19, 1999

[54] HEART STIMULATING DEVICE WITH STIMULATION ENERGY RESPONSIVE TO DETECTED NOISE

[75] Inventors: Martin Obel, Danderyd; Josef Vock, Spanga, both of Sweden

[73] Assignee: Pacesetter AB, Järfälla, Sweden

[21] Appl. No.: 20,737

[22] Filed: Feb. 9, 1998

[30] Foreign Application Priority Data

Feb. 10, 1997 [SE] Sweden .................................. 9700441
Jul. 4, 1997 [SE] Sweden .................................. 9702605

[51] Int. Cl.$^6$ .................................................. A61N 1/362
[52] U.S. Cl. ................................................ 607/11; 607/28
[58] Field of Search ......................... 607/11, 28; 128/901

[56] References Cited

U.S. PATENT DOCUMENTS

| 3,557,796 | 1/1971 | Keller et al. . | |
| 4,386,610 | 6/1983 | Leckrone . | |
| 4,779,617 | 10/1988 | Whigham .................................... | 607/9 |
| 4,969,460 | 11/1990 | Callaghan et al. . | |
| 5,431,693 | 7/1995 | Schroeppel ................................. | 607/28 |
| 5,531,772 | 7/1996 | Prutchi . | |

OTHER PUBLICATIONS

"Characteristics and Clinical Effects of Myopotential Signals in a Unipolar DDD Pacemaker Population," Zimmern et al., PACE, vol. 9, Nov.–Dec. 1986, Part II, pp. 1019–1025.
Pacesetter User Manual for Regency SC+, SC and SCX (1995).

Primary Examiner—William E. Kamm
Assistant Examiner—Kennedy J. Schaetzle
Attorney, Agent, or Firm—Hill & Simpson

[57] ABSTRACT

A heart stimulating device has pulse generators which can operate in either a first mode wherein the stimulation pulse energy is adjusted to a capture threshold of a patient's heart, or a second mode wherein the stimulation pulse energy is fixed. An evoked response detector senses IEGM signals to detect capture or non-capture subsequent to an emitted stimulation pulse. A noise detector detects as noise IEGM signals having predetermined signal characteristics. The noise detector, after having detected noise, sets the pulse generators to operate in the second mode. A lead arrangement connects the pulse generators, the evoked response detector, and the noise detector to a patient's heart.

22 Claims, 3 Drawing Sheets

HEART STIMULATING DEVICE WITH STIMULATION ENERGY RESPONSIVE TO DETECTED NOISE

BACKGROUND OF THE INVENTION

1. Field of the Invention

The present invention relates to a heart stimulating device having a capability to adapt its stimulation energy to the current capture threshold value in a patient's heart.

2. Description of the Prior Art

The invention concerns solutions to problems arising in sensing the activity of the heart when myopotential noise, external electromagnetic noise, or other noise is present.

Particularly, noise may severely affect sensing carried out with a unipolar lead connecting the heart and the stimulating device. For unipolar electrode systems the noise level is typically an order of magnitude higher than the noise level of bipolar electrode systems. Aggravating polarization problems may thus arise when stimulation and sensing employ the same polarity configuration, e.g., unipolar configuration.

Pacemakers may employ a unipolar or bipolar lead, i.e., a cardiac electrode arrangement plus a single or dual insulated wires or conductors connected to the pacemaker's connection terminal, for stimulating and sensing the activity of a patient's heart. A bipolar lead may be operated in bipolar or unipolar mode, but a unipolar lead can be operated only in unipolar mode.

Stimulation and sensing carried out on a common unipolar lead would be generally desirable provided that safety can be maintained. Two advantages of unipolar systems are the greater possibilities of using an already-implanted lead when the pacemaker needs to be replaced, and a lower number of components which may fail.

Some terminology used in this disclosure is explained below.

IEGM

An abbreviation for intracardiac electrogram. IEGM signals are emitted by active cardiac tissue and sensed through electrodes placed on or within the heart.

QRS or QRS complex

The ventricular depolarization as seen on the electrocardiogram or in the IEGM signals.

Intrinsic

Inherent or belonging to the heart itself. An intrinsic beat is a naturally occurring heartbeat.

Evoked response

The electrical activation of the myocardium caused by a pacemaker output pulse. The ability of heart cells to respond to a pacemaker output pulse depends on the extent to which the cells are in a refractory state.

Escape interval, basic interval, or basic escape interval

The period, typically of the order of 1000 milliseconds, between a sensed intrinsic cardiac event or a stimulation pulse output and the next pacemaker output pulse.

Lead

The insulated wire plus electrode(s) and terminal pin used to connect the pulse generator to cardiac tissue. The lead carries the stimulus from the pulse generator to the heart and, in demand modes, relays intrinsic cardiac signals back to the sense amplifier of the pulse generator. A single-chamber pulse generator requires one lead, while a dual-chamber pulse generator usually requires two (one for the atrium, another for the ventricle)

Bipolar lead

A pacing lead with two electrical poles that are external from the pulse generator. The negative pole or cathode is located at the extreme distal tip of the pacing lead, while the positive pole or anode is formed of an annular electrode located at a distance in the range of 10 millimeters from the cathode. The cathode is the electrode through which the stimulating pulse is delivered. Bipolar leads are characterized by relatively small spikes on the paced ECG.

Unipolar lead

A pacing lead with a single electrical pole at the distal tip of the pacing lead (negative pole). The anode (positive pole) is the pulse generator case. The cathode is the electrode through which the stimulating pulse is delivered. Unipolar stimulation or sensing via a unipolar lead is of course bipolar in the sense that, e.g., a conductive casing of the pacemaker constitutes a second pole.

Stimulation, capture, or pacing threshold

The minimum electric output from the pacemaker which consistently elicits a cardiac depolarization and contraction.

Stimulation energy

The energy of the electric output from the pacemaker. The energy is used herein to quantitatively describe the stimulation effectiveness of a stimulation pulse. Alternatively, it could be expressed in terms of voltage, current, width, shape, and/or charge of the pulse.

IEGM signal amplitude

The amplitude can be defined in two different ways: the peak value, i.e., the maximum distance (positive and/or negative) from the signal baseline, or the peak-to-peak value, i.e., the distance between the maximum positive and negative deflections of the IEGM signal. An implantable heart stimulating device usually senses the peak-to-peak value. Thus, a threshold for sensing could refer to either of these definitions.

In U.S. Pat. No. 4,969,460 a pacemaker is described having a spontaneous event and noise detector for sensing inter alia noise. When noise is detected a noise flag is set and capture detection and automatic output regulation is suspended (see e.g. col.24, lines 26–48). Instead pacing takes place with a comparatively large output. Criteria for setting the noise flag are not discussed.

The Pacesetter® REGENCY™ pacemaker with AUTOCAPTURE™, described in Pacesetter® User Manual, ordering no. 63 46 493 E500E, published in 1995, uses a bipolar arrangement connecting the pacemaker to the heart when operating in a mode wherein the stimulation pulse energy is adjusted in relation to the patient's changing capture threshold. In that AUTOCAPTURE mode, only one pole of the lead is used for delivering stimulation pulses, while both poles are used for sensing IEGM signals that are indicative of the heart's stimulation response and natural activity. In other modes of operation the pacemaker may be programmed to deliver stimulation pulses and sense heart activity in either bipolar or unipolar mode. The pacemaker may always completely inhibit a pulse, in order to favor natural heartbeats. In that way a long life of the battery-powered heart stimulating device may be achieved.

The adaptive function is advantageous, but to ensure correct evoked response (ER) detection, bipolar sensing is deemed absolutely necessary. In the described pacemaker, unipolar sensing could endanger correct ER detection, since that sensing is more sensitive to noise, especially myopotential, influence than bipolar sensing, as mentioned above. Depending on the sign and magnitude of the noise, ER sensing could erroneously indicate capture or non-capture, which could lead to an inappropriate reaction by the pacemaker.

Also, when sensing and stimulation are carried out with the same polarity, the sensing can be complicated due to polarization at the electrode(s) caused by the stimulation pulse, however, that is a problem not specifically related to the occurrence of noise.

If sensing and pulse adjustment based thereon could be performed reliably with a unipolar lead instead of a bipolar lead, one would also benefit from the advantages of a less complicated conductive means for transferring both the stimulation and sensing signals.

The general operation of a prior art pacemaker of the type initially described will now be described in greater detail.

Such a pacemaker operates in a sensing mode that incorporates a refractory period. Immediately following a pacemaker output or a sensed intrinsic event, the pacemaker ceases to be responsive to detectable signals for a predetermined period of time. This prevents the pulse generator from detecting the terminal portion of the depolarization signal and, in some circumstances, the repolarization signal which might result in timing errors.

In atrial applications, longer refractory periods should be employed to prevent detection of terminal portions of the QRS complex which, if detected, would reset the pulse generator timing, resulting in a lower pacing rate than the programmed rate.

The refractory period (=total refractory period) consists of a programmable absolute refractory period during which detection of all signals is blocked, and a non-programmable relative refractory (or noise-sampling) period (100 ms) during which detected signals cause a restart of the relative refractory period. Continuous detection of signals at a frequency of 10 Hz or more causes the pulse generator to revert to asynchronous operation at the programmed basic rate as long as noise is present. During periods of noise detection, the pulse generator stimulates at the programmed pulse amplitude and pulse width if the adjustment mode (AUTOCAPTURE™) is "OFF". If the adjustment mode is programmed "ON", the algorithm is interrupted and the output set to 4.5 V/0.49 ms to ensure pacing. High stimulation energy is necessary when the adjustment mode is "ON" because the noise will probably give false ER detections. As soon as the noise is absent, the pulse generator reverts to the normal inhibited mode with the same amplitude and pulse width as before the noise mode was entered, when operating in the adjustment mode. In this pacemaker, the noise is detected by the same circuit, with the same amplitude threshold, as used to sense heartbeats.

The programmable refractory periods, including the relative refractory period of 100 ms, range from 250 ms to 550 ms in steps of 50 ms.

Signals which occur at a frequency of 10 Hz or more are interpreted as noise and will cause the pacemaker to revert to asynchronous operation at the programmed rate while continuing to monitor for the presence of noise. This protects the patient by preventing the pacemaker from being totally inhibited by external interference.

Signals which occur at a frequency below 10 Hz have no effect upon pulse generator timing, unless the signal is detected during the normal sensing (or alert) period following the noise sampling period. Should this occur, pulse generator output either will be inhibited or triggered depending on the operating mode.

SUMMARY OF THE INVENTION

It is an object of the present invention to improve the prior art heart stimulating device and to provide a solution to its shortcomings regarding the use of an unipolar lead and, in particular, unipolar sensing.

The above object is achieved in accordance with the principles of the present invention in a heart stimulating device having a pulse generator which can operate in a first mode wherein stimulation pulses are emitted having a pulse energy which is adjusted relative to a varying capture threshold of the patient's heart, or in a second mode wherein stimulation pulses each having a predetermined energy are emitted, and evoked response detector which senses IEGM signals in order to detect capture or non-capture subsequent to an emitted stimulation pulse and which emits a corresponding detection signal, and a lead arrangement connecting the pulse generator and the evoked response detector to the patient's heart. The heart stimulating device of the invention also includes a noise detector which senses IEGM signals in order to detect noise IEGM signals having predetermined signal characteristics, the noise detector, after detecting noise, setting the pulse generator to operate in the second mode. The predetermined signal characteristics include an IEGM signal voltage which exceeds a predetermined threshold for a predetermined number of times during a time interval having a predetermined duration. The evoked response detector also employs a threshold, and the absolute value of the threshold employed by the noise detector is lower than the absolute value of the threshold employed by the evoked response detector. The pulse generator remains in the second mode for at least one basic interval subsequent to the detection of noise by the noise detector.

The lead arrangement also connects the noise detector to the patient's heart.

DESCRIPTION OF THE PREFERRED EMBODIMENTS

Effects relating to myopotentials have been documented, e.g., by Zimmern et al. in Characteristics and Clinical Effects of Myopotential Signals in a Unipolar DDD Pacemaker Population, PACE, Vol. 9, November–December, Part II, 1986. In their study, the authors conclude that knowledge of myopotential characteristics could allow pacemaker sensitivity settings to be chosen that prevent myopotentials from being erroneously detected as heartbeats. For that purpose, pacemakers were set up to record myopotentials. Average peak-to-peak maximum myopotential amplitudes were found to range between 0.9 and 1.0 mV for both atrial and ventricular unipolar sensing, while the measured maximum values were 1.9 and 2.2 mV, respectively. This article provides basic information on myopotential characteristics and effects in pacemaker applications.

Figure 3:
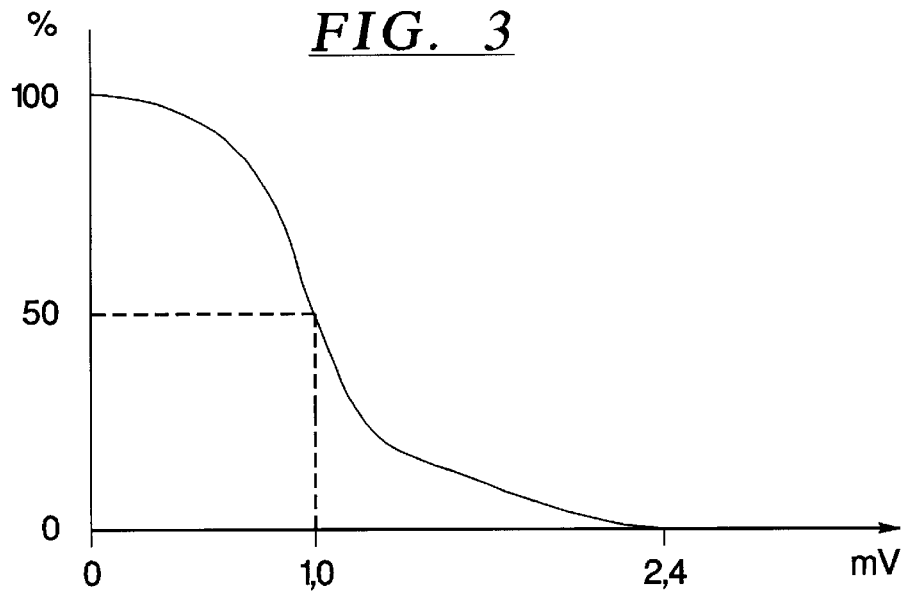
FIG. 3 is a diagram showing the probability of a myopotential amplitude as a function of the amplitude value.

FIG. 3 is a measurement-based diagram describing the probability of the occurrence of myopotentials versus myopotential amplitude. As seen in this diagram, a probability of a 1.0 mV amplitude is about 50% and the probability vanishes at about 2.4 mV.

Figure 1:
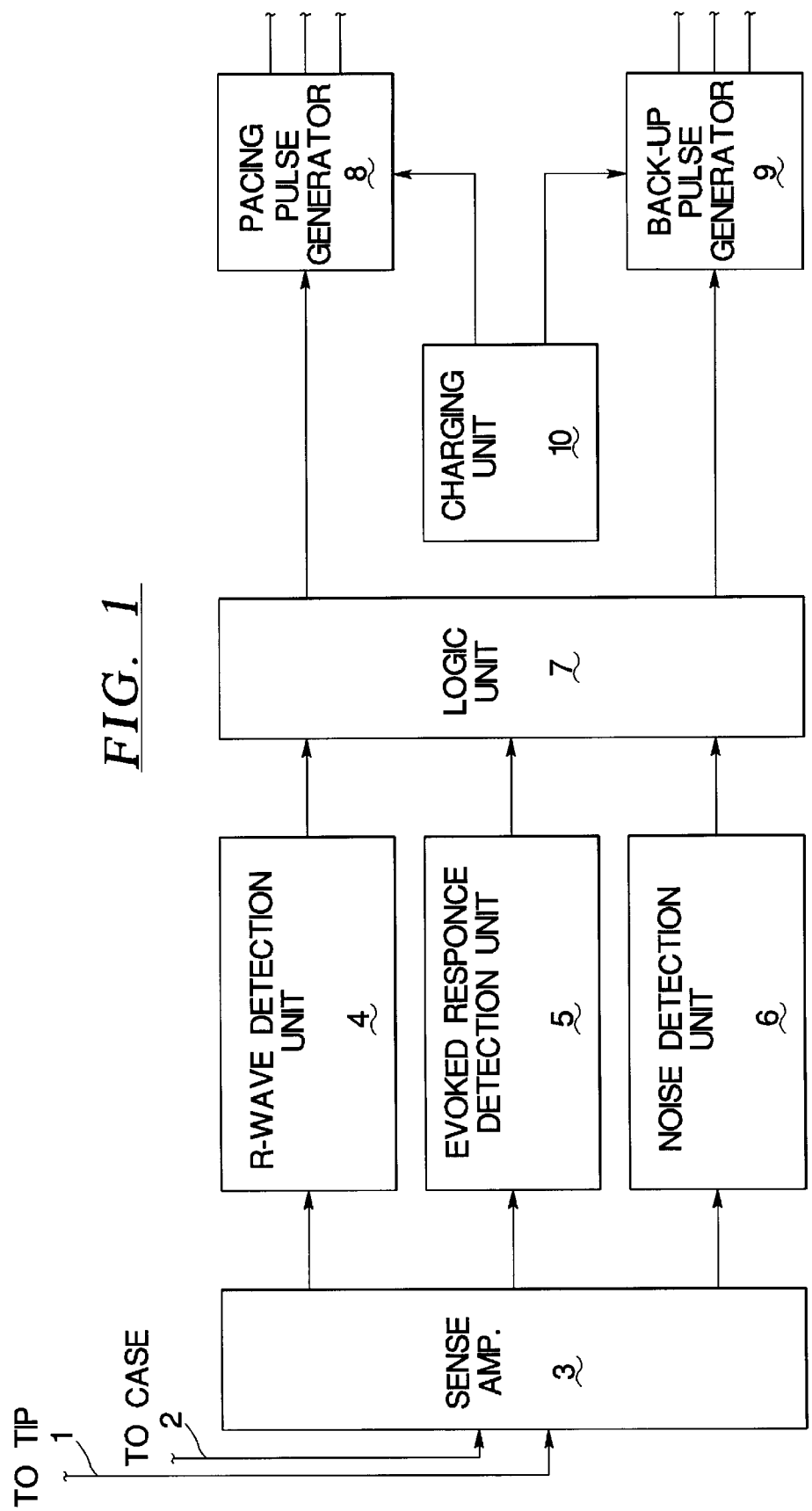
FIG. 1 is a block diagram of one embodiment of a heart stimulating device according to the invention.

To describe an embodiment of a heart stimulating device according the invention, reference is made to FIG. 1. The described type of device has unipolar stimulation and sensing and has two different modes of operation. In a first mode, the device detects evoked response and continuously adjusts the stimulation pulse energy so as to match a varying stimulation threshold of a patient's heart. In a second mode, the adjustment is turned off and the heart is paced at a fixed pulse energy (amplitude and duration), whenever the detection of the evoked response is considered less reliable due to noise of high amplitude being present in sensed IEGM signals.

Further, the device has sensing inputs 1 and 2 that feed IEGM signals to a sense amplifier 3 of the heart stimulating device. The first sensing input 1 is typically connected to a lead (not shown). The second sensing input 2 is typically connected to a housing of the device. The sense amplifier provides amplified IEGM signals to three detection units 4, 5 and 6. An R-wave detection unit 4 is operable to detect intrinsic QRS complexes, and may also have the ability to detect P waves if processing thereof is to be performed by the heart stimulating device. An evoked response (ER) detection unit 5 is operable to detect stimulation-evoked QRS complexes. A noise detection unit 6 is operable to detect the occurrence of noise in the IEGM signals. Each of the detection units 4, 5 and 6 is connected to a logic unit 7 to which it indicates a detected QRS complex or noise according to their respective functions.

The logic unit 7 controls a pacing pulse generator 8 and a back-up pulse generator 9 which are operable to transmit stimulation pulses to a patient's heart. The pulse generators 8 and 9 may be connected via the same lead (not shown) to the same cardiac electrode (not shown) as the sense amplifier 3. A charging unit 10 is connected to both pulse generators 8 and 9 to provide them with the necessary stimulation energy.

The logic unit 7 includes timing circuitry in order to stimulate the patient's heart at an appropriate rate when needed and to distinguish between the different detections made in the detection units 4, 5 and 6. The logic unit 7 may also deactivate any of the detection units 4, 5 or 6 during selected time intervals.

Figure 2:
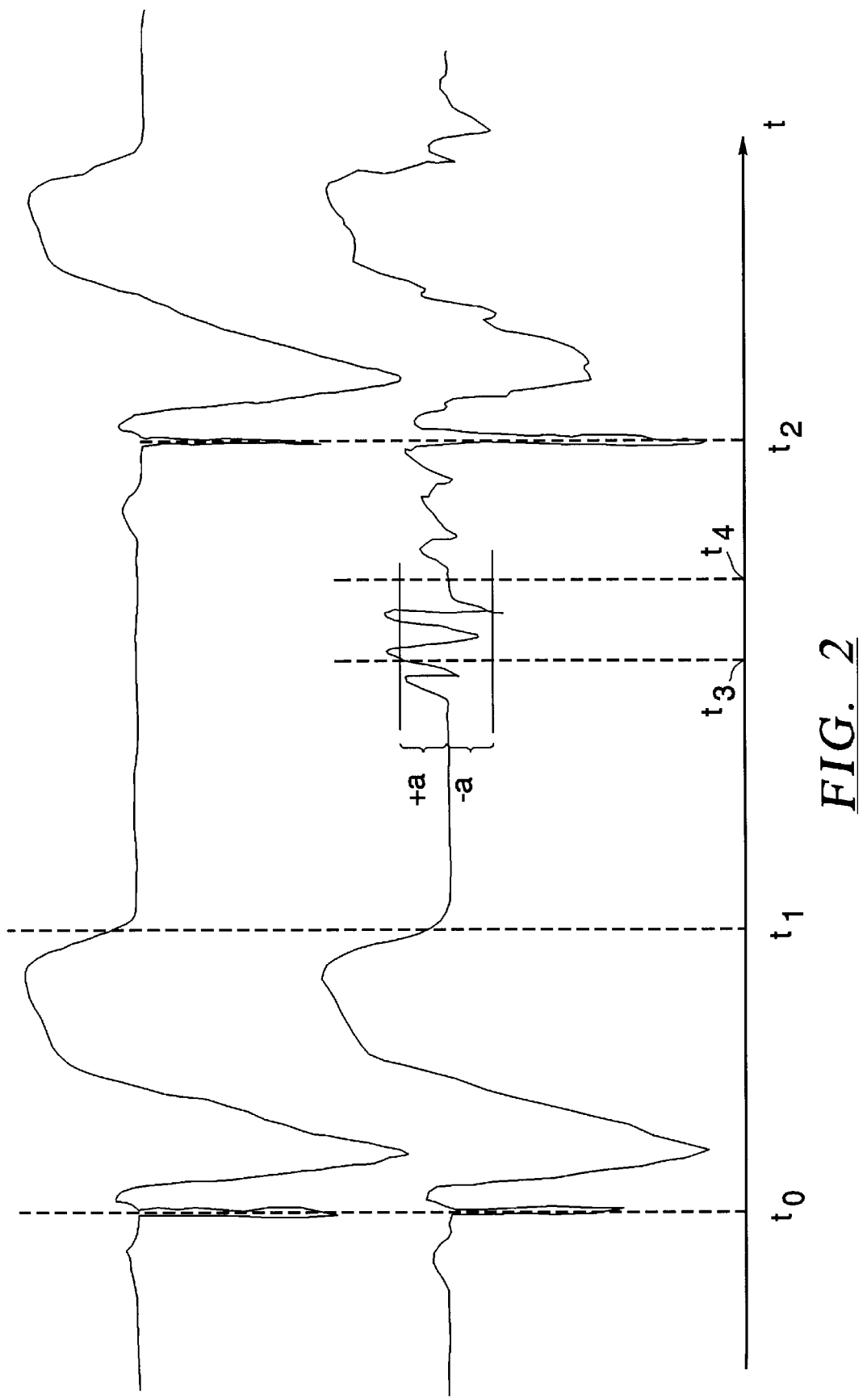
FIG. 2 shows an example of IEGM input signals to the device in FIG. 1 illustrating a noise-free situation and a situation where a myopotentials and other noise are intermittently present.

FIG. 2 includes an upper IEGM curve showing two consecutive stimulation-evoked QRS complexes and a lower IEGM curve similar to the upper one, but including also bursts of noise subsequent to the first stimulation-evoked QRS complex. As the noise bursts are detected by the noise detection unit 6, the logic unit 7 switches to the second mode of operation, wherein pulses of a fixed higher energy are delivered to the patient's heart.

In FIG. 2 times $t_0$, $t_1$, $t_2$, $t_3$, and $t_4$ have been marked with dashed lines to indicate an emission of a stimulation pulse to evoke a QRS ($t_0$), an end point of a time interval for sensing evoked response subsequent to a stimulation ($t_1$), an end of a basic interval at which a new stimulation pulse is emitted a first point of detection in the noise detection unit 6 of a noise amplitude exceeding a predetermined amplitude threshold +a ($t_3$), and an end of a noise detection interval wherein three noise amplitudes have been detected exceeding either the positive threshold +a or a negative amplitude threshold -a ($t_4$), respectively. As an example, the noise detection unit 6 indicates the presence of noise in case the IEGM signal amplitude exceeds a given amplitude at least three times within a predetermined time window.

In order to illustrate the operation of the inventive heart stimulating device a sequence to be described is assumed to start by the delivery of a stimulation pulse at $t_0$. Then the evoked response detection unit 5 is activated after a predetermined delay to detect evoked response until $t_1$. When an evoked response is detected in the absence of disturbing noise, as shown in the upper part of FIG. 2, the logic unit 7 maintains the first mode of operation. It may then lower the stimulation energy according to a predetermined adjustment algorithm, in order to adapt the stimulation energy in subsequent pulses to the stimulation threshold of the patient's heart. If no evoked response is detected, the heart stimulating device generally emits a back-up pulse. Also, non-capture is of course an important input to the adjustment algorithm.

At $t_2$, which is the end of the basic interval ranging from $t_0$ to $t_2$, the IEGM curves indicate a new stimulation pulse. The stimulation energy of the upper curve may then have been adjusted slightly, while the lower curve indicates operation in the second mode, wherein the stimulation pulse has a pulse energy substantially higher than that of the preceding pulse. In FIG. 2, both its amplitude and width have been increased, although the proportions are exaggerated, however, other combinations would be possible. In the second mode of operation, generally, the evoked response detection unit 5 is deactivated and, consequently, no back-up pulse can be delivered.

According to the invention, the noise detection unit 6, whose activation may be restricted to the time interval between sensed cardiac events, indicates the presence of noise to the logic unit 7 when certain signal characteristics are detected. In the example of FIG. 2 the noise detection unit 6 senses a first noise amplitude exceeding +a at $t_3$. A timer starts at and runs until $t_4$. The time interval between $t_3$ and $t_4$ may be 250 ms. In that interval, the noise detection unit 6 detects two other noise amplitudes reaching outside the amplitude interval from -a to +a. Subsequent to detection of the third amplitude peak, the noise detection unit 6 will indicate the presence of noise to the logic unit 7, which in turn can respond by switching to the second mode of operation.

The logic unit 7, however, will normally ignore any indication from the noise detection unit 6 if the R-wave detection unit 4 indicates the presence of an intrinsic event. In that case the logic unit 7 inhibit the next stimulation pulse. Each of the three detection units 4, 5, and 6 may include a signal level detector (for detection through the filtered IEGM signal) having a respective threshold. The threshold in the noise detection unit 6 is the lowest and that of the evoked response unit 5 and the R-wave detection unit 4 have a higher threshold.

A safe and long operation of the inventive heart stimulating 10 device is effectively maintained since it is only the presence of disturbing noise that automatically deactivates the continuous adjustment of the stimulation energy. The higher pulse energy is intended to be used in exceptional situations only so that the extra energy consumption in the second mode can be expected to be very small, over the entire life of the heart stimulating device.

It has been estimated to be sufficient and advantageous for the pulse generator to remain in the second mode for 10–50 stimulation pulses subsequent to a most recent detection of noise in the noise detection means. An interval of 1–5000 stimulation pulses, however, seems to be an interval wherein energy preservation and safety can still be maintained by the inventive device. Moreover, in order to save energy when in the second mode, the noise detection unit 6 may be temporarily disabled and the presence of noise presumed.

It should be noted that FIG. 2 is not drawn to scale but rather illustrates the relative timing and magnitude of typical phenomena monitored through the IEGM signals.

Figure 4:
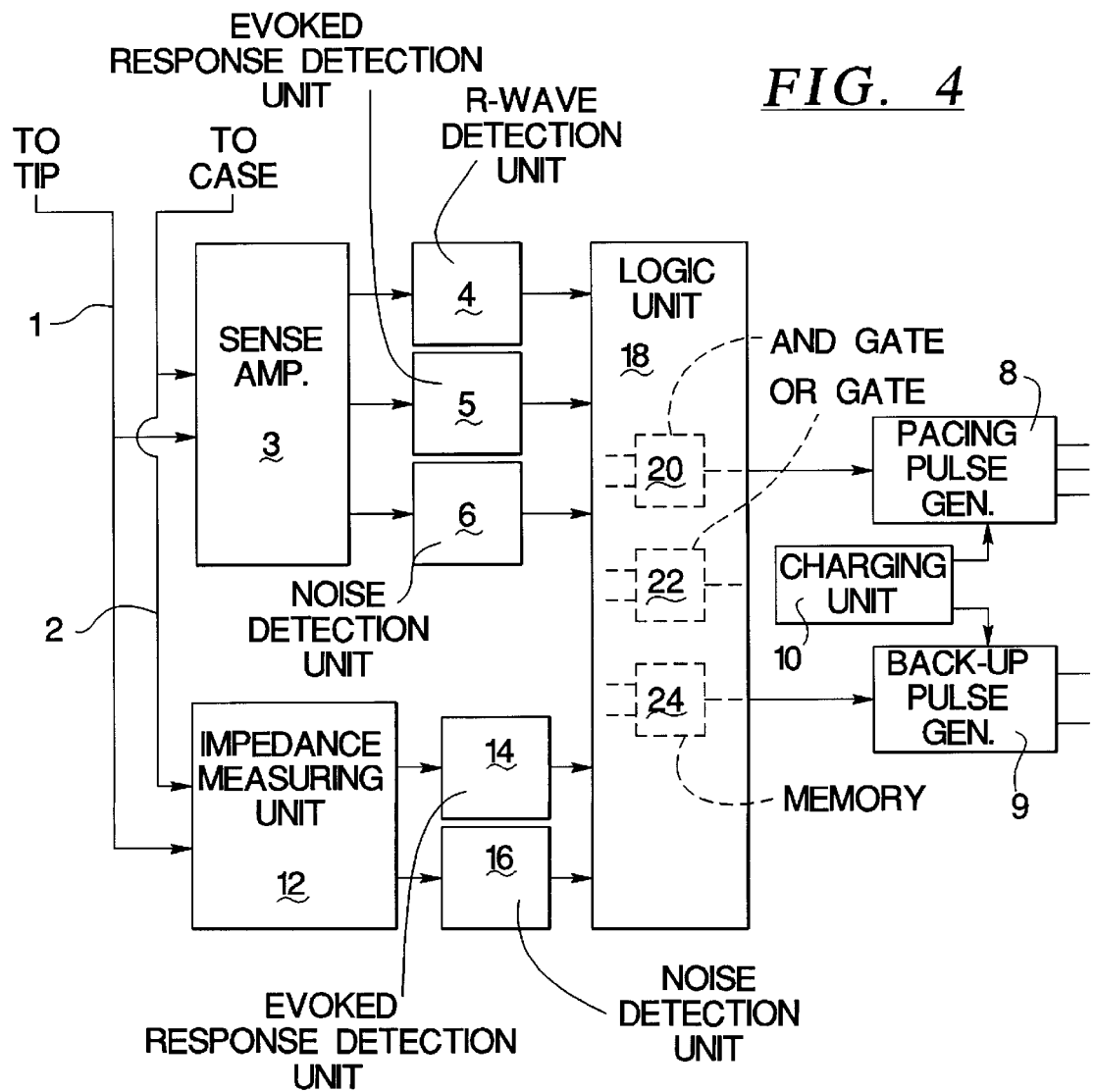
FIG. 4 is a block diagram of an alternative embodiment of the heart stimulating device according to the invention.

FIG. 4 shows a block diagram of a further embodiment of the embodiment of the heart stimulating device according to the invention. In the embodiment shown in FIG. 4 the sensing inputs 1 and 2 are connected not only to the sense amplifier 3 for providing an amplified IEGM-signal, as described in connection with FIG. 1, but also to an impedance measuring unit 12 for measurement of the total impedance between the electrode tip and the stimulator case. The impedance measuring unit 12 delivers amplified impedance signals to an evoked response detection unit 14 and a noise detection unit 16. The evoked response detection unit 14 is operable to detect stimulation evoked response from changes in the measured impedance reflecting contraction and relaxation of the heart and the noise detection unit 16 is operable to detect the occurrence of noise in the impedance signals.

The impedance measurements are performed a certain number of times during a pacing cycle, e.g. at intervals of the order of 10–30 msec. For the measurements relatively short, high current measuring pulses are used. The pulse length is typically 10–30 μsec and the pulse current intensity is on the order of mA.

Each of the detection units 14 and 16 is connected to a logic unit 18. This logic unit 18 essentially corresponds to the logic unit 7 in FIG. 1. Output signals from the three detection unit 4, 5 and 6 are also supplied to this logic unit 18.

The logic unit 18 controls the pacing pulse generator 8 and back-up pulse generator 9 according to information received from the five detection units 4, 5 ,6, 14 and 16. Different criteria or algorithms can be used in the logic unit 18 for making decisions from the input signal information for how to control the pulse generators 8 and 9. Also in this embodiment an indication from the R-wave detection unit 4 of the presence of an intrinsic event will result in an inhibition of the next stimulation pulse, regardless of the indications from the noise detection means 6 and 16. The logic unit 18 can further include an AND-gate 20 connected at its inputs to the two evoked response detection units 5 and 14 for delivering an output signal indicating capture only if both these detection units 5 and 14 indicate capture, whereas all other possible situations are interpreted as loss of capture or noise. This improves the safety in the detection of capture and gives a very robust, noise resistant and reliable detection of capture.

If e.g. the IEGM signal indicates evoked response but the 5 impedance signal does not, there is a risk that polarization disturbances or other kinds of disturbances are detected as an evoked response in the IEGM measurement. This risk of false detection is eliminated with this embodiment of the device according to the invention.

The logic unit 18 can also include e.g. an OR-gate 22 connected at its inputs to the noise detection units 6 and 16 for delivering an output noise signal for control of the generators 8 and 9 if one of the two noise detection units 6 or 16 indicates the presence of noise. Noise can be detected in the same way as described in connection with FIG. 2.

Also other logic combinations of the information from the signals from the detection units 4, 5, 6, 14 and 16 can be realized in the logic unit 18 for obtaining an optimal control of the pulse generators 8 and 9.

The impedance measurement values reflect the contraction and relaxation of the hearth as mentioned above and the response is therefore relatively slow. The blood filling of the heart is influencing the impedance, and the T-wave constitutes the proof for the relaxation of the heart. An evaluation period of up to a few hundred milliseconds is necessary before a capture or loss of capture information is available. The logic unit 18 therefore includes a memory 24 for storing at least the information from the impedance measurement from the preceding pacing cycle for combining this stored information from the preceding cycle with information from the IEGM measurements of the ongoing pacing cycle. As an alternative, information both from the IEGM measurement and the impedance measurements can be stored in the memory 24 and used in the logic unit 18 together with information from the IEGM measurement of the ongoing pacing cycle for the evoked response or loss of capture decision.

Thus, in the embodiment according to FIG. 4 information from 5 both IEGM measurements and impedance measurements are combined in a decision logic which in its turn controls a suitable AUTOCAPTURE™ algorithm. The impedance measurement then provides additional safety and constitutes an acknowledgment whether or not sensed evoked response or loss of capture is correct or not.

The noise detection units 6 and 16 are operating also when the pulse generator 9 is delivering back-up pulses for stopping the pulse generator 9 and triggering the pulse generator 8 when a noiseless state is detected.

The logic unit 7 (or 18) can automatically cause the pulse generator 8 to revert to operation in the first mode following a predetermined time after entry into the second mode.

The addition of the impedance measurement is of particular value for heart stimulating devices of the unipolar type, however, the impedance measurements can also be used in heart stimulators of bipolar type for detecting heart movements.

It is to be understood that this embodiment description includes merely illustrative examples of the application of the invention. Thus, many further variations and modifications may be made without departing from the scope of the invention as defined by the appended claims. For example, noise could be detected by comparing the IEGM signal to a predetermined noise morphology template.

Although modifications and changes may be suggested by those skilled in the art, it is the intention of the inventors to embody within the patent warranted hereon all changes and modifications as reasonably and properly come within the scope of their contribution to the art.

We claim as our invention:

1. A heart stimulating device comprising:

pulse generator means for emitting stimulation pulses, said pulse generator means being operable in a first mode for producing stimulation pulses respectively having a pulse energy adjusted relative to a varying capture threshold of a heart, and in a second mode for emitting stimulation pulses each having a predetermined energy;

lead means connected to said pulse generator means, and adapted for connection to the heart, for delivering said stimulation pulses to the heart and for assisting in obtaining IEGM signals from the heart;

evoked response detection means connected to said lead means for sensing said IEGM signals and for emitting a capture detection signal indicating capture subsequent to an emitted stimulation pulse, dependent on a relationship of said IEGM signals to a first threshold;

noise detection means connected to said lead means for detecting noise having a predetermined signal characteristics in said IEGM signals, said predetermined signal characteristics including an IEGM signal voltage which exceeds a second threshold of said noise detection means for a predetermined number of times during a time interval having a predetermined duration, said second threshold having an absolute value which is lower than an absolute value of said first threshold, said noise detection means emitting a noise detection signal if said IEGM signal voltage exceeds said second threshold; and logic means, supplied with said capture detection signal and said noise detection signal and connected to said pulse generator means, for causing said pulse generator means to operate in said first mode as long as said capture detection signal is present and for causing said pulse generator means to operate in said second mode if said capture detection signal is absent or if said noise detection signal is present.

2. A heart stimulating device as claimed in claim 1 wherein said logic means comprises means, if said pulse generator means in said second mode, for maintaining said pulse generator means in said second mode for at least one stimulation pulse subsequent to receipt of said noise detection signal.

3. A heart stimulating device as claimed in claim 1 wherein said noise detection means comprises means for detecting noise IEGM signals having an IEGM signal morphology similar to a predetermined morphology template.

4. A heart stimulating device as claimed in claim 1 wherein said noise detection means comprises means for detecting said noise in said IEGM signals if said IEGM signal amplitude exceeds 0.25 mV at three times within a time interval of 250 msec.

5. A heart stimulating device as claimed in claim 1 further comprising a housing containing said pulse generator means, said evoked response detection means, said noise detection means and said logic means, wherein said lead means includes a tip electrode, and wherein said evoked response detection means comprises first evoked response detection means, and said heart stimulating device further comprising second evoked response detection means for measuring an impedance between said tip electrode and said housing and for emitting a further detection signal, dependent on the measured impedance, indicating capture subsequent to an emitted stimulation pulse, and wherein said logic means is also supplied with said further detection signal and comprises means for logically combining said detection signal and said further detection signal to produce a logic result, and for operating said pulse generator means in said first mode or in said second mode dependent on said logic result.

6. A heart stimulating device as claimed in claim 5 wherein said logic means comprises an AND-gate supplied with said detection signal and said further detection signal and for operating said pulse generator means in said first mode only if both of said detection signal and said further detection signals are present.

7. A heart stimulating device as claimed in claim 6 wherein said logic means comprises memory means connected to said first and second evoked response detection means for storing information regarding capture and non-capture from at least one preceding pacing cycle, and wherein said means for logically combining comprises means for logically combining said information in said memory with said detection signals from said first and second evoked response detection means for a current pacing cycle.

8. A heart stimulating device as claimed in claim 5 wherein said second evoked response detection means comprises means for measuring said impedance a plurality of times during a pacing cycle.

9. A heart stimulating device as claimed in claim 8 wherein said second evoked response detection means comprises means for measuring said impedance at intervals predetermined (e.g. in a range between 10 and 30 msec).

10. A heart stimulating device as claimed in claim 8 wherein said second evoked response detection means comprises means for measuring said impedance during a period having a predetermined duration (e.g. in a range between 10 and 30 $\mu$sec).

11. A heart stimulating device as claimed in claim 5 wherein said second noise detection means comprises means for detecting noise impedance signals having predetermined signal characteristics and for emitting a noise impedance detection signal as said further detection signal, and wherein said logic means comprises means for logically combining said first and second detection signals and said noise IEGM signal and said noise impedance signal for controlling operation of said pulse generator means.

12. A heart stimulating device as claimed in claim 11 wherein said means for combining comprises an AND-gate connected to said first and second noise detection means for setting said pulse generator means to operate in said second mode only if said AND-gate is supplied with both said detection signal and said noise impedance signal.

13. A heart stimulating device as claimed in claim 11 wherein said means for combining comprises an OR-gate connected to said first and second noise detection means for setting said pulse generator means to operate in said second mode if supplied with either one of said detection signal or said noise impedance signal.

14. A heart stimulating device as claimed in claim 5 wherein each of said first and second noise detection means has an evoked-response sensing interval associated therewith, and each of said first and second noise detection means operating only outside of said evoked-response sensing interval.

15. A heart stimulating device as claimed in claim 5 wherein each of said evoked response detection means, said first noise detection means and said second noise detection means has a sensitivity, and wherein the sensitivity of each of said first noise detection means and said second noise detection means is higher than the sensitivity of said evoked response detection means.

16. A heart stimulating device as claimed in claim 1 further comprising Intrinsic event detection means, connected to said lead means, for detecting an intrinsic cardiac event and for thereupon supplying an intrinsic event detection signal to said logic means, said logic means comprising means, upon receipt of said intrinsic event detection signal for controlling said pulse generator means for Inhibiting emission of a stimulation pulse.

17. A heart stimulating device as claimed in claim 16 wherein said logic means comprises means for inhibiting emission of a stimulation pulse independently of whether said noise detection means emits said noise detection signal.

18. A heart stimulating device as claimed in claim 16 wherein said intrinsic event detection means has a third threshold associated therewith for use in detecting whether an intrinsic cardiac event has occurred, said third threshold having an absolute value between the absolute value of said first threshold and the absolute value of said second threshold.

19. A heart stimulating device as claimed in claim 1 wherein said logic means comprises means, If said pulse generator means is operating in said second mode, for causing said pulse generator means to revert to operation in said first mode following a predetermined time subsequent to a beginning operation in said second mode.

20. A heart stimulating device as claimed in claim 1 wherein said pulse generator means comprises means in said second mode for emitting said stimulation pulses at said predetermined stimulation energy which is a fixed value.

21. A heart stimulating device as claimed in claim 20 wherein said fixed value comprises a first fixed value, and wherein said pulse generator means comprises means for emitting said stimulation pulses at said predetermined stimulation energy in said second mode equal to a sum of a most recent stimulation energy plus a second fixed value.

22. A heart stimulating device as claimed in claim 21 wherein said lead means comprises a unipolar lead.

* * * * *